(12) United States Patent
Johnson

(10) Patent No.: US 9,357,719 B2
(45) Date of Patent: Jun. 7, 2016

(54) SQUASH HYBRID SV0104YL AND PARENTS THEREOF

(71) Applicant: SEMINIS VEGETABLE SEEDS, INC., St. Louis, MO (US)

(72) Inventor: William C. Johnson, Sacramento, CA (US)

(73) Assignee: Seminis Vegetable Seeds, Inc., Woodlands, CA (US)

( * ) Notice: Subject to any disclaimer, the term of this patent is extended or adjusted under 35 U.S.C. 154(b) by 556 days.

(21) Appl. No.: 13/764,767

(22) Filed: Feb. 11, 2013

(65) Prior Publication Data

US 2014/0157446 A1 Jun. 5, 2014

Related U.S. Application Data

(60) Provisional application No. 61/732,187, filed on Nov. 30, 2012.

(51) Int. Cl.
*A01H 5/08* (2006.01)

(52) U.S. Cl.
CPC ........................................ *A01H 5/08* (2013.01)

(58) Field of Classification Search
None
See application file for complete search history.

(56) References Cited

U.S. PATENT DOCUMENTS 7,432,420 B2 * 10/2008 Johnson et al. ............... 800/310
8,288,617 B2 10/2012 Johnson

OTHER PUBLICATIONS

U.S. Appl. No. 11/761,877, Johnson.
Moose SP, Mumm RH., "Molecular plant breeding as the foundation for 21st century crop improvement", Plant Physiol.; 147(3):969-77; Jul. 2008.
Ukraine Application for Plant Variety Rights, filed Nov. 30, 2012. Variety specific information as indicated in transmittal letter of Mar. 25, 2014 Information Disclosure Statement for U.S. Appl. No. 13/764,767.

* cited by examiner

*Primary Examiner* — Anne Kubelik
(74) *Attorney, Agent, or Firm* — Dentons US LLP; Alissa Eagle, Esq.

(57) ABSTRACT

The invention provides seed and plants of squash hybrid SV0104YL and the parent lines thereof. The invention thus relates to the plants, seeds and tissue cultures of squash hybrid SV0104YL and the parent lines thereof, and to methods for producing a squash plant produced by crossing such plants with themselves or with another squash plant, such as a plant of another genotype. The invention further relates to seeds and plants produced by such crossing. The invention further relates to parts of such plants, including the fruit and gametes of such plants.

32 Claims, No Drawings

SQUASH HYBRID SV0104YL AND PARENTS THEREOF

CROSS-REFERENCE TO RELATED APPLICATIONS

This application claims the priority of U.S. Provisional Appl. Ser. No. 61/732,187, filed Nov. 30, 2012, the entire disclosure of which is incorporated herein by reference.

FIELD OF THE INVENTION

The present invention relates to the field of plant breeding and, more specifically, to the development of squash hybrid SV0104YL and the inbred squash lines ZGN-EH10010 and LEB-EH-08-001.

BACKGROUND OF THE INVENTION

The goal of vegetable breeding is to combine various desirable traits in a single variety/hybrid. Such desirable traits may include any trait deemed beneficial by a grower and/or consumer, including greater yield, resistance to insects or disease, tolerance to environmental stress, and nutritional value.

Breeding techniques take advantage of a plant's method of pollination. There are two general methods of pollination: a plant self-pollinates if pollen from one flower is transferred to the same or another flower of the same plant or plant variety. A plant cross-pollinates if pollen comes to it from a flower of a different plant variety.

Plants that have been self-pollinated and selected for type over many generations become homozygous at almost all gene loci and produce a uniform population of true breeding progeny, a homozygous plant. A cross between two such homozygous plants of different genotypes produces a uniform population of hybrid plants that are heterozygous for many gene loci. Conversely, a cross of two plants each heterozygous at a number of loci produces a population of hybrid plants that differ genetically and are not uniform. The resulting non-uniformity makes performance unpredictable.

The development of uniform varieties requires the development of homozygous inbred plants, the crossing of these inbred plants, and the evaluation of the crosses. Pedigree breeding and recurrent selection are examples of breeding methods that have been used to develop inbred plants from breeding populations. Those breeding methods combine the genetic backgrounds from two or more plants or various other broad-based sources into breeding pools from which new lines and hybrids derived therefrom are developed by selfing and selection of desired phenotypes. The new lines and hybrids are evaluated to determine which of those have commercial potential.

SUMMARY OF THE INVENTION

In one aspect, the present invention provides a squash plant of the hybrid designated SV0104YL, the squash line ZGN-EH10010 or squash line LEB-EH-08-001. Also provided are squash plants having all the physiological and morphological characteristics of such a plant. Parts of these squash plants are also provided, for example, including pollen, an ovule, scion, a rootstock, a fruit, and a cell of the plant.

In another aspect of the invention, a plant of squash hybrid SV0104YL and/or squash lines ZGN-EH10010 and LEB-EH-08-001 comprising an added heritable trait is provided. The heritable trait may comprise a genetic locus that is, for example, a dominant or recessive allele. In one embodiment of the invention, a plant of squash hybrid SV0104YL and/or squash lines ZGN-EH10010 and LEB-EH-08-001 is defined as comprising a single locus conversion. In specific embodiments of the invention, an added genetic locus confers one or more traits such as, for example, herbicide tolerance, insect resistance, disease resistance, and modified carbohydrate metabolism. In further embodiments, the trait may be conferred by a naturally occurring gene introduced into the genome of a line by backcrossing, a natural or induced mutation, or a transgene introduced through genetic transformation techniques into the plant or a progenitor of any previous generation thereof. When introduced through transformation, a genetic locus may comprise one or more genes integrated at a single chromosomal location.

The invention also concerns the seed of squash hybrid SV0104YL and/or squash lines ZGN-EH10010 and LEB-EH-08-001. The squash seed of the invention may be provided as an essentially homogeneous population of squash seed of squash hybrid SV0104YL and/or squash lines ZGN-EH10010 and LEB-EH-08-001. Essentially homogeneous populations of seed are generally free from substantial numbers of other seed. Therefore, seed of hybrid SV0104YL and/or squash lines ZGN-EH10010 and LEB-EH-08-001 may be defined as forming at least about 97% of the total seed, including at least about 98%, 99% or more of the seed. The seed population may be separately grown to provide an essentially homogeneous population of squash plants designated SV0104YL and/or squash lines ZGN-EH10010 and LEB-EH-08-001.

In yet another aspect of the invention, a tissue culture of regenerable cells of a squash plant of hybrid SV0104YL and/or squash lines ZGN-EH10010 and LEB-EH-08-001 is provided. The tissue culture will preferably be capable of regenerating squash plants capable of expressing all of the physiological and morphological characteristics of the starting plant, and of regenerating plants having substantially the same genotype as the starting plant. Examples of some of the physiological and morphological characteristics of the hybrid SV0104YL and/or squash lines ZGN-EH10010 and LEB-EH-08-001 include those traits set forth in the tables herein. The regenerable cells in such tissue cultures may be derived, for example, from embryos, meristems, cotyledons, pollen, leaves, anthers, roots, root tips, pistils, flowers, seed and stalks. Still further, the present invention provides squash plants regenerated from a tissue culture of the invention, the plants having all the physiological and morphological characteristics of hybrid SV0104YL and/or squash lines ZGN-EH10010 and LEB-EH-08-001.

In still yet another aspect of the invention, processes are provided for producing squash seeds, plants and fruit, which processes generally comprise crossing a first parent squash plant with a second parent squash plant, wherein at least one of the first or second parent squash plants is a plant of squash line ZGN-EH10010 or squash line LEB-EH-08-001. These processes may be further exemplified as processes for preparing hybrid squash seed or plants, wherein a first squash plant is crossed with a second squash plant of a different, distinct genotype to provide a hybrid that has, as one of its parents, a plant of squash line ZGN-EH10010 or squash line LEB-EH-08-001. In these processes, crossing will result in the production of seed. The seed production occurs regardless of whether the seed is collected or not.

In one embodiment of the invention, the first step in "crossing" comprises planting seeds of a first and second parent squash plant, often in proximity so that pollination will occur for example, mediated by insect vectors. Alternatively, pollen can be transferred manually. Where the plant is self-pollinated, pollination may occur without the need for direct human intervention other than plant cultivation.

A second step may comprise cultivating or growing the seeds of first and second parent squash plants into plants that bear flowers. A third step may comprise preventing self-pollination of the plants, such as by emasculating the flowers (i.e., killing or removing the pollen).

A fourth step for a hybrid cross may comprise cross-pollination between the first and second parent squash plants. Yet another step comprises harvesting the seeds from at least one of the parent squash plants. The harvested seed can be grown to produce a squash plant or hybrid squash plant.

The present invention also provides the squash seeds and plants produced by a process that comprises crossing a first parent squash plant with a second parent squash plant, wherein at least one of the first or second parent squash plants is a plant of squash hybrid SV0104YL and/or squash lines ZGN-EH10010 and LEB-EH-08-001. In one embodiment of the invention, squash seed and plants produced by the process are first generation ($F_1$) hybrid squash seed and plants produced by crossing a plant in accordance with the invention with another, distinct plant. The present invention further contemplates plant parts of such an $F_1$ hybrid squash plant, and methods of use thereof. Therefore, certain exemplary embodiments of the invention provide an $F_1$ hybrid squash plant and seed thereof.

In still yet another aspect, the present invention provides a method of producing a plant derived from hybrid SV0104YL and/or squash lines ZGN-EH10010 and LEB-EH-08-001, the method comprising the steps of: (a) preparing a progeny plant derived from hybrid SV0104YL and/or squash lines ZGN-EH10010 and LEB-EH-08-001, wherein said preparing comprises crossing a plant of the hybrid SV0104YL and/or squash lines ZGN-EH10010 and LEB-EH-08-001 with a second plant; and (b) crossing the progeny plant with itself or a second plant to produce a seed of a progeny plant of a subsequent generation. In further embodiments, the method may additionally comprise: (c) growing a progeny plant of a subsequent generation from said seed of a progeny plant of a subsequent generation and crossing the progeny plant of a subsequent generation with itself or a second plant; and repeating the steps for an additional 3-10 generations to produce a plant derived from hybrid SV0104YL and/or squash lines ZGN-EH10010 and LEB-EH-08-001. The plant derived from hybrid SV0104YL and/or squash lines ZGN-EH10010 and LEB-EH-08-001 may be an inbred line, and the aforementioned repeated crossing steps may be defined as comprising sufficient inbreeding to produce the inbred line. In the method, it may be desirable to select particular plants resulting from step (c) for continued crossing according to steps (b) and (c). By selecting plants having one or more desirable traits, a plant derived from hybrid SV0104YL and/or squash lines ZGN-EH10010 and LEB-EH-08-001 is obtained which possesses some of the desirable traits of the line/hybrid as well as potentially other selected traits.

In certain embodiments, the present invention provides a method of producing food or feed comprising: (a) obtaining a plant of squash hybrid SV0104YL and/or squash lines ZGN-EH10010 and LEB-EH-08-001, wherein the plant has been cultivated to maturity, and (b) collecting at least one squash from the plant.

In still yet another aspect of the invention, the genetic complement of squash hybrid SV0104YL and/or squash lines ZGN-EH10010 and LEB-EH-08-001 is provided. The phrase "genetic complement" is used to refer to the aggregate of nucleotide sequences, the expression of which sequences defines the phenotype of, in the present case, a squash plant, or a cell or tissue of that plant. A genetic complement thus represents the genetic makeup of a cell, tissue or plant, and a hybrid genetic complement represents the genetic make up of a hybrid cell, tissue or plant. The invention thus provides squash plant cells that have a genetic complement in accordance with the squash plant cells disclosed herein, and seeds and plants containing such cells.

Plant genetic complements may be assessed by genetic marker profiles, and by the expression of phenotypic traits that are characteristic of the expression of the genetic complement, e.g., isozyme typing profiles. It is understood that hybrid SV0104YL and/or squash lines ZGN-EH10010 and LEB-EH-08-001 could be identified by any of the many well known techniques such as, for example, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science,* 280:1077-1082, 1998).

In still yet another aspect, the present invention provides hybrid genetic complements, as represented by squash plant cells, tissues, plants, and seeds, formed by the combination of a haploid genetic complement of a squash plant of the invention with a haploid genetic complement of a second squash plant, preferably, another, distinct squash plant. In another aspect, the present invention provides a squash plant regenerated from a tissue culture that comprises a hybrid genetic complement of this invention.

Any embodiment discussed herein with respect to one aspect of the invention applies to other aspects of the invention as well, unless specifically noted.

The term "about" is used to indicate that a value includes the standard deviation of the mean for the device or method being employed to determine the value. The use of the term "or" in the claims is used to mean "and/or" unless explicitly indicated to refer to alternatives only or the alternatives are mutually exclusive. When used in conjunction with the word "comprising" or other open language in the claims, the words "a" and "an" denote "one or more," unless specifically noted otherwise. The terms "comprise," "have" and "include" are open-ended linking verbs. Any forms or tenses of one or more of these verbs, such as "comprises," "comprising," "has," "having," "includes" and "including," are also open-ended. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits.

Other objects, features and advantages of the present invention will become apparent from the following detailed description. It should be understood, however, that the detailed description and any specific examples provided, while indicating specific embodiments of the invention, are given by way of illustration only, since various changes and modifications within the spirit and scope of the invention will become apparent to those skilled in the art from this detailed description.

DETAILED DESCRIPTION OF THE INVENTION

The invention provides methods and compositions relating to plants, seeds and derivatives of squash hybrid SV0104YL, also known as LEBEHH0104, squash line ZGN-EH10010 and squash line LEB-EH-08-001.

Squash hybrid SV0104YL is a long Lebanese-type squash with high levels of vigor and disease resistance. SV0104YL features intermediate level resistance to ZYMV, WMV, and SLCV. Fruit shape is uniformly cylindrical, with the color preferred in multiple markets.

SV0104YL is well adapted for commercial production in North Africa, Eastern Europe, and parts of Asia. Variety performance is most valuable in seasons with disease pressure from potyvirus and/or geminivirus diseases.

A. ORIGIN AND BREEDING HISTORY OF SQUASH HYBRID SV0104YL

The parents of hybrid SV0104YL are ZGN-EH10010 and LEB-EH-08-001. These parents were created as follows:

Squash line LEB-EH-08-001 is an inbred parent line developed from a complex selection strategy involving multiple starting components. These include 1) ZGY-46-2604, the original gray zucchini source of resistance to SLCV, which was distributed by Sergio Garza from the Universidad de Sonora in Hermosillo, Sonora, Mexico, in 1998, 2) A selection from the landrace of Lebanese type squash collected in Turkey before 1980 known as "beyaz kabak," 3) a single plant selection from a diverse early generation population of squash distributed by Henry Munger of Cornell University in 1986 as "ZUCX85-187-3" to collaborating seed companies and initially designated as "HMZYR" (presumably representing Henry Munger ZYMV resistant family), 4) a local landrace of squash known locally as "calabacita" from Morelos, Mexico, and collected by the author 5) the commercial hybrid "Eskenderany", 6) "C88," a public germplasm accession available from the French agricultural research agency known as NRA, 7) a selection from the cultivated landrace "Small Green Algerian," and 8) "Verde Milano Migliorato," a long green zucchini type cultivar from Italy.

In late 1986 three segregating early generation (BC2F1) populations of potyvirus resistant squash families were shared from Henry Munger at Cornell University. One of these was designated as "ZUCX85-187-3" and 20 seeds were distributed for increase and germplasm exchange with the Petoseed company breeding operation in Felda, Fla. An individual plant from this family was selected and used as a male parent in a cross with a selection from the "Small Green Algerian" landrace. The F1 seed from this cross was self pollinated, and between 1987 and 1992 was advanced to the F8 generation at breeding nurseries in New Jersey and Florida, guided by progeny testing results with ZYMV and WMV screening. In 1993 this breeding line was again crossed to a selection from the "Small Green Algerian" landrace in California. The F1 generation was self pollinated in a greenhouse without selection, and the resulting F2 population was inoculated with a cocktail of ZYMV and WMV in 1994. Survivors from this screen were selected for conformity to the grey zucchini ideotype (compact, productive plant with tapered fruit and a diffuse, green net on immature fruits). This screen was repeated in 1995 on the F3 generation. In 1996 the F4 and F5 generations were grown and self pollinated without phenotypic selection in the greenhouse and in Felda, Fla. In 1997 the F6 population was again inoculated with ZYMV and WMV, and one survivor was hybridized to a selection of the "Small Green Algerian" landrace (effectively a BC2F1). In late 1997 this new hybrid was self pollinated in the greenhouse without phenotypic selection. In 1998 and 1999 the F2 and F3 generations were each inoculated with ZYMV and WMV, and survivors were selected based on conformity to the grey zucchini ideotype. In late 1999 and in 2000 the F4 and F5 generations were grown and self pollinated without phenotypic selection. In 2001 the F6 generation was inoculated with ZYMV and observed to be uniformly resistant, and uniform for a fruit and plant type similar to the grey zucchini ideotype. A single plant from this F6 generation was self pollinated.

The F7 progeny was hybridized in 2002 to ZGY-46-2604, and the resulting F1 hybrid was sown near Hermosillo, Mexico. This hybrid was observed to be somewhat resistant to SLCV under conditions of natural infection. A nearby plot of the Mexican landrace "calabacita" showed exceptional earliness, and was used as the male parent to create a new hybrid (F1×landrace=new F1 segregating population). This variable F1 population was planted in Woodland Calif. in early 2003 and the seedlings were artificially inoculated with both ZYMV and SLCV. Survivors from that screen were moved to the greenhouse and self pollinated. The F2 population was planted in late 2003 near Hermosillo Mexico with heavy natural infestation of SLCV, and individual resistant plants were selected and self pollinated. The F3 generation was selected for use as a male parent to generate a new population targeting the Lebanese phenotype in 2004, and was crossed to the proprietary inbred line LEB-47-5004.

Proprietary inbred line LEB-47-5004 also traces lineage back to "HMZYR". In 1986 a different individual plant selection from the diverse F1 family known as ZUCX85-187-3 was also crossed to the landrace "Small Green Algerian." This lineage followed the same path as described previously between generations F1 and F7 (one less generation) between 1987 and 1992. In 1994 an F7 selection from this alternate lineage was artificially inoculated at Woodland Calif. with ZYMV, and the family was observed to be uniformly resistant. A surviving plant from that screen was used as the female parent in a cross to a selection of the landrace "beyaz kabak", and the resulting F1 hybrid was self pollinated at a greenhouse in Woodland, Calif. In 1995 the F2 generation was inoculated with ZYMV, and survivors were selected for conformity to the Lebanese ideotype (white fruit color, thick leaves, strong canopy, high vigor). The same screen was repeated on the F3 generation in 1996. The F4 and F5 generations were selected and self pollinated based only on phenotypic conformity to the Lebanese ideotype. In 1997 four individual plants from the F6 generation showing phenotypic uniformity were selected and bulked to create the proprietary inbred line LEB-47-5004.

Again returning to the narrative above from 2004, when the F3 generation was selected and crossed to LEB-47-5004, in early 2005 this new F1 population was artificially inoculated with SLCV. One of the surviving individuals was selected for use as a female parent in a new breeding population, targeting Lebanese type fruit with longer, more cylindrical fruit. This selected F1 individual was hybridized to the proprietary breeding line A829.

Proprietary breeding line A829 was developed in Nimes, France, and Tifton, Ga., USA. A829 shows acceptable levels of resistance to ZYMV, and was derived from 6 generations of self pollination following hybridization between "C88" and an inbred line derived from the commercial hybrid "Eskenderany", with selection for conformity to the long Lebanese ideotype (white fruit color, cylindrical elongated shape, high productivity, early maturity, bush type growth habit). This long Lebanese type inbred was then crossed to a selection of the "Verde Milano Migliorato" cultivar (presumably to increase the fruit length of the Lebanese type parent), then self pollinated for six generations with phenotypic selection for conformity to the long Lebanese type ideotype and resistance to ZYMV observed in natural infections. This long Lebanese type breeding line was then itself crossed to a different inbred selection of "Eskenderany," and six additional generations of self pollination were performed, to create the breeding line A829.

Again returning to the narrative above, from the hybridization between the diverse F1 population to A829: in late 2005 this new F1 generation family was artificially inoculated with SLCV, and a single resistant individual was selected and self pollinated. The F2 generation was sent to Nimes, France for observation in early 2006, and was selected there for conformity to the Lebanese ideotype for a single generation. Selected self pollinated F3 families were again artificially inoculated with SLCV, and the survivors were self pollinated in the greenhouse at Woodland Calif. in late 2006. In 2007 the F4 generation was again artificially inoculated with SLCV, and survivors self-pollinated in the greenhouse. The F5 generation was planted and self pollinated, without phenotypic selection, and the progeny of a single plant was designated as the finished inbred line known as LEB-EH-08-001.

ZGN-EH10010, the male parent of SV0104YL, was also developed through a complex breeding strategy involving multiple components: 1) ZGN-130-1003, a proprietary breeding line contributing fruit quality characteristics and some potyvirus resistance that is itself derived directly from six generations of inbreeding of the commercial hybrid "Tigress", (2) ZGY-46-2604, the original gray zucchini source of resistance to SLCV, which was distributed by Sergio Garza from the Universidad de Sonora in Hermosillo, Sonora, Mexico, in 1998, (3) G710, a proprietary breeding line contributing fruit quality characteristics, derived directly from the commercial hybrid "Black Beauty", (4) HP13HMW/HP134*1, a breeding line contributing high resistance to ZYMV, WMV-2, and PRSV, and which was previously described in the patent for parent line ZGN-130-1028 (5) Tamino, a cultivated landrace popular in Italy, (6) "ZUCX85-187-3," previously described above as part of the ancestry of LEB-EH-08-001, and (7) ZGN-47-134, a proprietary breeding line which can be made available for distribution. ZGN-EH10010 is derived from germplasm with high levels of resistance to SLCV, an unexpected result of the combination of low levels of resistance from ZGY 46-2604 and the SLCV susceptible breeding line HP13HMW/HP134*1, which is the subject of different intellectual property filings, U.S. patent application Ser. No. 10/761,877 and U.S. Pat. No. 8,288,617 (U.S. patent application Ser. No. 12/197,908).

In late 1986 three segregating early generation (BC2F1) populations of potyvirus resistant squash families were shared from Henry Munger at Cornell University. One of these was designated as "ZUCX85-187-3" and 20 seeds were distributed for increase and germplasm exchange with the Petoseed company breeding operation in Felda, Fla. An individual plant from this family was selected and used as a male parent in a cross with a selection from the "Tamino" landrace. The F1 seed from this cross was self pollinated, and between 1987 and 1992 was advanced to the F8 generation at breeding nurseries in New Jersey and Florida, guided by progeny testing results with ZYMV and WMV screening. In 1993 an inbred selection from this population was crossed to the proprietary breeding line ZGN-47-134.

The F1 generation with male parent ZGN-47-134 was self pollinated in a greenhouse without selection, and the resulting F2 population was inoculated with a cocktail of ZYMV and WMV in 1994. F3 survivors from this screen were planted again in the same screen in 1995, and survivors were selected for conformity to the ZGN ideotype (medium green cylindrical fruit, vigorous habit, upright growth, high productivity) and self pollinated. F4 selections were planted in late 1995 in Felda, Fla., and selected for conformity to the ZGN ideotype. In 1996 the F5 generation was again inoculated with ZYMV and WMV, and observed to be uniformly resistant. An individual plant selection from this generation was selected and self pollinated, and in 1997 a generation advancement from the F6 to F7 generation was made. In 1998 a single F7 selection was again planted in the greenhouse, and a bulk of phenotypically uniform plants was made to create the proprietary inbred line ZGN-47-5011.

In 2000, a new hybrid was created by crossing ZGN-130-1003 (itself an F7 derived directly from the commercial hybrid "Tigress") to ZGN-47-5011. This hybrid was evaluated for its potential as a commercial hybrid and ultimately rejected, but was appreciated for the combination of vigor, fruit quality, and productivity. In 2001 this hybrid was self pollinated to create a new source of breeding germplasm. The F2 generation from this cross was sown in Felda, Fla. in early 2002, and selected for conformity to the green zucchini ideotype. The F3 generation was artificially inoculated with a cocktail of ZYMV, WMV, and PRSV, and survivors were selected and self pollinated in summer, 2002. This screen was repeated in 2003 on the F4 generation. The F5 generation was sown in Felda, Fla., and selected for conformity to the green zucchini ideotype in late 2003 and self pollinated. An individual plant from the F5 generation was selected for use in the F6 generation as the parent of new hybrids, and was hybridized in early 2004 to a series of male parent lines. One of those male parent lines was the F5 generation selection from the TAW population that will be described now. The parent lines used to develop ZGN-EH10010 were hybridized in early 2004, the above section refers to the female lineage, and the below selection refers to the male lineage.

ZGY-46-2604 was crossed to a series of breeding lines, including G710, in order to develop breeding populations with a combination of SLCV resistance and acceptable green zucchini fruit types in 1998. The resulting F1 progeny of this cross was backcrossed to G710, and the BC1F2, BC1F3, and BC1F4 generations were selected for fruit and plant characteristics without regard to SLCV virus resistance in Tifton, Ga.

The self-pollinated BC1F5 progeny selections were included in a field trial in the Rio Grande Valley of Texas in late summer 2000 (a location and date chosen for its history of SLCV epidemics). Heavy SLCV pressure and high levels of potyvirus infestations in the same field allowed for the selections of breeding lines with SLCV and potyvirus resistance. Nineteen selections (or remnant seed in the case of failed pollinations) were chosen to be planted in the greenhouse at Woodland, Calif. in February, 2001 and inoculated with SLCV. Four BC1F5 and BC1F6 families were selected for a high level of resistance to SLCV and for fruit quality characteristics.

The selected families were crossed to a series of thirty-one diverse breeding lines in the spring of 2001, including ZGN-130-1003. During the summer of 2001, these breeding lines were evaluated for virus resistance through individual and cocktail screens of potyviruses and for fruit quality characteristics in Woodland, Calif. Ten hybrids were selected, and these ten hybrids were subsequently evaluated for resistance to SLCV in a nursery planted in Hermosillo, Mexico in the latter part of 2001. The hybrid (ZGN-130-1003/(ZGY-46-2604/G710*1)) was selected for development of new germplasm. This hybrid was planted in the greenhouse at Woodland, Calif. in February of 2002, and was crossed to proprietary inbred line HP13HMW/HP134*1.

The resulting F1 population, known as (ZGN-130-1003/(ZGY-46-2604/G710*1F6))/(HP13HMW/HP134*1), was inoculated with a cocktail of ZYMV, WMV-2, and PRSV, and survivors were moved to the field in Woodland, Calif. in the summer of 2002. This survivor population and all its F2 and subsequent progeny were named TAW. Thirty-seven individuals were selected from the TAW population based on potyvirus resistance and fruit and plant characteristics. The F2 generations from these thirty seven selections were sown in the greenhouse in Woodland, Calif. in January 2003, and inoculated with ZYMV, WMV-2, PRSV, and SLCV.

The high SLCV resistance described was first observed in this early 2003 screen, where F2 individuals in certain families showed much higher levels of resistance to SLCV than the original source of resistance, ZGY-46-2604. These F2 individuals were self-pollinated.

F3 families derived from the F2 individuals with unexpectedly high levels of SLCV resistance were inoculated with a cocktail of ZYMV, WMV-2, and PRSV, and resistant individuals were transplanted to a field near Woodland, Calif. in the summer of 2003. One hundred and two F3 individuals were selected for self-pollination from this field based on their level of potyvirus resistance, and fruit and plant characteristics. Successful progeny from the California F3 generation were sown in Florida in late 2003 to evaluate fruit quality, and also in Sinaloa (for a simultaneous observation under heavy potyvirus and geminivirus natural pressure), and F4 families were selected and self pollinated. The field trial in Sinaloa allowed verification of the high level geminivirus resistance in an environment very similar to a commercial field. The selected lines provided a verification of the unexpected results from the early 2003 greenhouse screen, because the F4 generation also showed a higher level of resistance to natural geminivirus infection than the genotype which was the original source of resistance. The F5 generation was sown the greenhouse at Woodland Calif. in early 2004 to generate new hybrid combinations with commercial potential. A single individual from the F6 generation of this population was later designated as ZGN-130-1028, but it is unlikely that the lineage leading to ZGN-EH10010 is from the same individual plant in the F5 generation that led to ZGN-130-1028. The male parent of ZGN-EH10010 and the lineage leading to ZGN-130-1028 likely diverged in the F5 generation.

The hybrid created in early 2004, described above, was observed in field trials in the summer of 2004. Based on initial observations, it was selected for further population development, although the hybrid itself never resulted in a successful commercial product, and has subsequently been dropped from further evaluation. The F2 population was generated in late 2004 from self pollination of hybrid plants in a greenhouse. In early 2005, 144 F2 seedlings were artificially inoculated with SLCV, and 42 surviving plants were transferred to the greenhouse. 31 of those plants generated F3 families, which where sown in summer, 2005 and inoculated with a cocktail of ZYMV, WMV, and ZYMV. Resistant plants were observed in ten of those F3 families, and individual plants were selected and self pollinated. In early 2006 the F4 generation was inoculated with SLCV, and survivors were transferred to the greenhouse and self pollinated. The F5 generation was inoculated with a cocktail of ZYMV, WMV, and PRSV in 2006, and was observed to be resistant and phenotypically uniform prior to self pollination. The F6 generation was sown in a greenhouse for amplification, and a single F7 generation individual as self pollinated and designated as the source of parent line ZGN-EH10010 in early 2009.

SV0104YL was first created in 2009, and first observed in a hybrid trial in Turkey in late 2009. The hybrid was observed to have uniform cylindrical fruit shape, strong plant performance when observed under high natural infection pressure of potyvirus, and acceptable fruit color and yield.

The parent lines are uniform and stable, as is a hybrid produced therefrom. A small percentage of variants can occur within commercially acceptable limits for almost any characteristic during the course of repeated multiplication. However no variants are expected.

B. PHYSIOLOGICAL AND MORPHOLOGICAL CHARACTERISTICS OF SQUASH HYBRID SV0104YL, SQUASH LINE ZGN-EH10010 AND SQUASH LINE LEB-EH-08-001

In accordance with one aspect of the present invention, there is provided a plant having the physiological and morphological characteristics of squash hybrid SV0104YL and the parent lines thereof. A description of the physiological and morphological characteristics of such plants is presented in Tables 1-3.

TABLE 1

Physiological and Morphological Characteristics of Hybrid SV0104YL

| CHARACTERISTIC | SV0104YL | Comparison Variety Anita |
|---|---|---|
| 1. Species | *Pepo* | *Pepo* |
| 2. Kind/Use | squash | squash |
| 3. Type | summer (vegetable marrow) | summer |
| 4. Cotyledon | | |
| length | 46.5 mm | 42.55 mm |
| width | 29.9 mm | 28.55 mm |
| apex | tapered | tapered |
| veining | plainly visible | plainly visible |
| color | medium green | medium green |
| color (RHS Color Chart) | 137B | 137A |
| Seedling | | |
| shape of cotyledons | elliptic (Cora, Tivoli) | elliptic |
| intensity of green color of cotyledons | medium (Cora) | medium |
| cross section of cotyledons | concave | straight |

TABLE 1-continued Physiological and Morphological Characteristics of Hybrid SV0104YL

| CHARACTERISTIC | SV0104YL | Comparison Variety Anita |
|---|---|---|
| 5. Mature Plant | | |
| growth habit | bush | semi-bush |
| plant type | glabrous | pilose |
| 6. Main Stem | | |
| cross-section shape | angled | round |
| diameter at mid-point of 1st internode | 28.3 mm | 26.15 mm |
| average length | 33 cm | 45.8 cm |
| average number of internodes | 33.8 | 33 |
| Stem | | |
| color | completely green (Becky) | partly green and partly yellow |
| intensity of green color | dark (Greyzini) | very dark |
| mottling | present (Cora) | absent |
| tendrils | absent to rudimentary (Goldrush, Sylvana) | well developed |
| Plant | | |
| growth habit | bush (Greyzini) | semi-trailing |
| branching | absent (Goldi) | absent |
| bush varieties only: attitude of petiole (excluding lower external leaves) | erect to semi-erect (Sardane) | |
| 7. Leaves | | |
| blade shape | reniform | reniform |
| blade form | deep lobed | deep lobed |
| margin | dentate | denticulate |
| margin edges | frilled | frilled |
| average width | 38.9 cm | 36.2 cm |
| average length | 31.3 cm | 29.75 cm |
| leaf surface | blistered | blistered |
| dorsal surface pubescence | glabrous | glabrous |
| vental surface pubescence | glabrous | glabrous |
| color | dark green | dark green |
| color (RHS Color Chart) | 147A | 147A |
| leaf blotching | blotched with gray | blotched with gray |
| leaf blade: size | medium (Ambassador) | large |
| leaf blade: incisions | medium (Jackpot) | medium |
| leaf blade: intensity of green color of upper surface | dark (Everest) | dark |
| leaf blade: silvery patches | present (Civac) | present |
| leaf blade: relative area covered by silvery patches | medium (Ambassador) | small |
| average petiole length | 39.3 cm | 38.35 cm |
| petiole length | long (Autumn Gold, Baikal) | long |
| petiole: number of prickles | medium (Spidy) | few |
| 8. Flower | | |
| pistillate flower: average diameter | 17.6 cm | 15.9 cm |
| pistillate flower: ovary | drum-like | drum-like |
| pistillate flower: average pedicel length | 1.5 cm | 1.7 cm |
| pistillate flower: margin shape | curved | curved |
| pistillate flower: margin edges | frilled | frilled |
| pistillate flower: average sepal width | 1.5 mm | 1.35 mm |
| pistillate flower: average sepal length | 3.1 mm | 5.4 mm |
| pistillate flower: color | orange | orange |
| pistillate flower: color (RHS Color Chart) | 23A | 23A |
| staminate flower: average sepal length | 14.5 mm | 16.8 mm |
| staminate flower: average sepal width | 3.3 mm | 3 mm |
| staminate flower: average pedicel length | 130 mm | 122.9 mm |
| staminate flower: color | orange | orange |

TABLE 1-continued

Physiological and Morphological Characteristics of Hybrid SV0104YL

| CHARACTERISTIC | SV0104YL | Comparison Variety Anita |
|---|---|---|
| female flower: ring at inner side of corolla | present (Aurore) | present |
| female flower: color of ring at inner side of corolla | green (Aurore, Early White Bush Scallop, President) | green |
| female flower: intensity of green color of ring at inner side of corolla (varieties with green ring at inner side of corolla) | medium (Samba, Senator) | medium |
| male flower: ring at inner side of corolla | present (Goldi) | present |
| male flower: color of ring at inner side of corolla | green (Austral, Belor, Goldi) | green |
| male flower: intensity of green color of ring at inner side of corolla | strong (Goldi) | medium |
| staminate flower: color | 23A | 17A |
| 9. Fruit | | |
| market maturity: average length | 15.7 cm | 13.3 cm |
| market maturity: average width - stem end | 2.2 cm | 3.1 cm |
| at market maturity: average width - blossom end | 0.9 cm | 3 cm |
| market maturity: average weight | 215.4 gm | 236.5 gm |
| market maturity: shape according to variety type | straightneck | straightneck |
| market maturity: apex | rounded | flattened |
| market maturity: base | rounded | rounded |
| market maturity: ribs | inconspicuous | inconspicuous |
| market maturity: rib furrow depth | shallow | shallow |
| market maturity: rib furrow width | narrow | narrow |
| market maturity: fruit surface | smooth | smooth |
| market maturity: warts | none | none |
| market maturity: blossom scar button | raised acorn | raised acorn |
| young fruit: ratio length/ maximum diameter (zucchini type varieties) | large (Carlotta) | medium |
| young fruit: general shape (zucchini and rounded zucchini type varieties) | tapered elliptical (Top Kapi) | tapered elliptical |
| young fruit: main color of skin (excluding color of ribs or grooves) | green (Elite, Opal, Romano) | green |
| young fruit: intensity of green color of skin (excluding color of ribs or grooves; only varieties with green color of skin) | very light (Clarita, Goya, Patty Green Tint) | light |
| general shape | club shaped | club shaped |
| length (zucchini type varieties) | medium (Cora) | medium |
| maximum diameter (zucchini type varieties) | medium (Opal) | medium |
| ratio length/maximum diameter (zucchini type varieties) | medium (Cora) | medium |
| blossom end (zucchini and neck type varieties) | rounded | rounded |
| grooves | absent | absent |
| ribs | present | present |
| protrusion of ribs | very weak (Leda, Tivoli) | weak |
| main color of skin (excluding color of dots, patches, stripes and bands) | green (Ambassador, Baby Bear) | green |
| intensity of green color of skin (only varieties with green color of skin) | very light | light |

TABLE 1-continued

Physiological and Morphological Characteristics of Hybrid SV0104YL

| CHARACTERISTIC | SV0104YL | Comparison Variety Anita |
|---|---|---|
| stripes in grooves | | absent |
| color of ribs compared to main color of skin | same (Grey Zucchini) | same |
| dots | present (Gold Rush, Table Queen) | present |
| size of main dots | medium (Grey Zucchini) | small |
| secondary green color between ribs (excluding dots) | absent (Grey Zucchini, Small Sugar) | absent |
| warts on skin | absent | absent |
| size of flower scar | small (Goldi) | large |
| length of peduncle | medium (Cinderella) | medium |
| color of peduncle | green (Ambassador) | green |
| intensity of green color of peduncle | medium (Sunburst) | medium |
| mottling of peduncle | present (Elite) | absent |
| ripe fruit: secondary color of skin (excluding color of mottles, patches, stripes and bands) | yellow (Gold Rush) | yellow |
| ripe fruit: intensity of main color of skin (only yellow and orange) | medium | light |
| ripe fruit: color of flesh | cream (Elite) | cream |
| ripe fruit: lignified rind | present (Elite, Little Gem, Scallopini, Yellow Summer Crookneck) | present |
| ripe fruit: structure of flesh | fibrous (Vegetable Spaghetti) | fibrous |
| 10. Rind | | |
| average thickness at medial | 2.4 mm | 2.5 mm |
| toughness | hard | hard |
| overall color pattern | regular | regular |
| main or ground color | yellow | yellowish orange |
| main or ground color (RHS Color Chart) | 13B | 18A |
| 11. Flesh | | |
| average blossom end thickness | 44.1 mm | 29.45 mm |
| average medial thickness | 44.3 mm | 52.8 mm |
| average stem end thickness | 41.4 mm | 26.25 mm |
| texture (fine, granular, lumpy or stringy) | granular | fine |
| texture (soft, firm or brittle) | soft | firm |
| texture (dry, moist or juicy) | juicy | juicy |
| flavor | insipid | sweet |
| quality | good | excellent |
| color | creamy white | |
| color (RHS Color Chart) | 150D | 157D |
| 12. Seed Cavity | | |
| average length | 27.6 cm | 25.5 cm |
| average width | 5.8 cm | 8.7 cm |
| location | conforms to fruit shape | conforms to fruit shape |
| placental tissue | abundant | abundant |
| center core | inconspicuous | inconspicuous |
| 13. Fruit Stalks | | |
| average length | 2.7 cm | 3.15 cm |
| average diameter | 1.9 cm | 2.1 cm |
| cross-section shape | irregular | irregular |
| twisting | twisted | not twisted |
| tapering | tapered | tapered |
| straightness | slightly curved | straight |
| texture | hard | soft |
| furrows | deep | shallow |
| surface | rough | spiny |
| attachment end | slightly expanded | expanded |
| detaches | with difficulty | easily |
| color | medium green | medium green |
| color (RHS Color Chart) | 141B | 143B |

TABLE 1-continued

Physiological and Morphological Characteristics of Hybrid SV0104YL

| CHARACTERISTIC | SV0104YL | Comparison Variety Anita |
|---|---|---|
| 14. Seeds | | |
| average length | 15.7 mm | 18.6 mm |
| average width | 8.9 mm | 9.2 mm |
| average thickness | 3.2 mm | 2.8 mm |
| face surface | wrinkled | smooth |
| color | cream | white |
| color (RHS Color Chart) | 11C | 155A |
| luster | dull | dull |
| margin | straight | curved |
| margin edge | wedge-like | rounded |
| separation from pulp | moderately easy | easy |
| average grams per 100 seeds | 14 gm | 17 gm |
| average number of seeds per fruit | 352 | 342 |
| seed coat | normal | normal |
| size | medium (Diamant) | large |
| shape | broad elliptic (Baby Boo) | elliptic |
| hull | present (Baby Bear, Elite) | present |
| appearance of hull | fully developed (Elite) | fully developed |
| color of hull | cream (De Nice à Fruit Rond) | cream |
| fruit type: | zucchini | |
| fruit: patches, stripes or bands in ripe stage (if zucchini type) | absent (Ambassador, Black Jack) | |

*These are typical values. Values may vary due to environment. Other values that are substantially equivalent are also within the scope of the invention.

TABLE 2

Physiological and Morphological Characteristics of Line ZGN-EH10010

| CHARACTERISTIC | ZGN-EH10010 | Comparison Variety PAYROLL |
|---|---|---|
| 1. Species | *Pepo* | *Pepo* |
| 2. Kind/Use | squash | squash |
| 3. Type | summer (vegetable marrow) | summer |
| 4. Cotyledon | | |
| length | 45.3 mm | 45.5 mm |
| width | 28.2 mm | 29.25 mm |
| apex | rounded | tapered |
| veining | plainly visible | obscure |
| color | medium green | medium green |
| color (RHS Color Chart) | 137B | 137A |
| Seedling | | |
| shape of cotyledons | elliptic (Cora, Tivoli) | elliptic |
| cross section of cotyledons | convex (Bianchini, Yellow Crookneck) | concave |
| 5. Mature Plant | | |
| growth habit | bush | bush |
| plant type | pilose | pilose |
| 6. Main Stem | | |
| cross-section shape | angled | round |
| diameter at mid-point of 1$^{st}$ internode | 27.1 mm | 23.4 mm |
| average length | 30.5 cm | 30.75 cm |
| average number of internodes | 31.4 | 24.2 |
| Stem | | |
| color | completely green (Becky) | completely green |
| intensity of green color | dark (Greyzini) | dark |
| mottling | absent (Cinderella) | absent |
| tendrils | absent to rudimentary (Goldrush, Sylvana) | well developed |

TABLE 2-continued

Physiological and Morphological Characteristics of Line ZGN-EH10010

| CHARACTERISTIC | ZGN-EH10010 | Comparison Variety PAYROLL |
|---|---|---|
| Plant | | |
| growth habit | bush (Greyzini) | bush |
| branching | absent (Goldi) | absent |
| bush varieties only: attitude of petiole (excluding lower external leaves) | semi-erect (Arlesa) | erect |
| 7. Leaves | | |
| blade shape | reniform | reniform |
| blade form | deep lobed | deep lobed |
| margin | denticulate | dentate |
| margin edges | frilled | frilled |
| average width | 33.7 cm | 32.4 cm |
| average length | 28.3 cm | 29.1 cm |
| leaf surface | blistered | blistered |
| dorsal surface pubescence | soft hairy | soft hairy |
| vental surface pubescence | soft hairy | soft hairy |
| color | dark green | dark green |
| color (RHS Color Chart) | 147A | 139A |
| leaf blotching | blotched with gray | blotched with gray |
| leaf blade: size | medium (Ambassador) | small |
| leaf blade: incisions | deep (Civac) | deep |
| leaf blade: intensity of green color of upper surface | dark (Everest) | dark |
| leaf blade: silvery patches | present (Civac) | present |
| leaf blade: relative area covered by silvery patches | medium (Ambassador) | small |
| average petiole length | 30.1 cm | 35.15 cm |
| petiole length | medium (Goldi) | long |
| petiole: number of prickles | medium (Spidy) | few |
| 8. Flower | | |
| pistillate flower: average diameter | 16.1 cm | 15.3 cm |
| pistillate flower: ovary | drum-like | drum-like |
| pistillate flower: average pedicel length | 1.4 cm | 1.75 cm |
| pistillate flower: margin shape | curved | straight |
| pistillate flower: margin edges | frilled | frilled |
| pistillate flower: average sepal width | 1.1 mm | 1.25 mm |
| pistillate flower: average sepal length | 2.6 mm | 5.25 mm |
| pistillate flower: color | orange | orange |
| pistillate flower: color (RHS Color Chart) | 23A | 17A |
| staminate flower: average sepal length | 13.1 mm | 18.5 mm |
| staminate flower: average sepal width | 2.7 mm | 2.95 mm |
| staminate flower: average pedicel length | 140.2 mm | 175 mm |
| staminate flower: color | orange | orange |
| female flower: ring at inner side of corolla | present (Aurore) | present |
| female flower: color of ring at inner side of corolla | yellow and green (Pueble) | green |
| male flower: ring at inner side of corolla | present (Goldi) | present |
| male flower: color of ring at inner side of corolla | yellow and green (Alice, Carmina, Green Gem, Ibis) | green |
| staminate flower: color | 23A | 21A |
| 9. Fruit | | |
| market maturity: average length | 19.1 cm | 19.05 cm |
| market maturity: average width - stem end | 2.1 cm | 3.2 cm |
| at market maturity: average width - blossom end | 1.1 cm | 1.8 cm |

TABLE 2-continued

Physiological and Morphological Characteristics of Line ZGN-EH10010

| CHARACTERISTIC | ZGN-EH10010 | Comparison Variety PAYROLL |
|---|---|---|
| market maturity: average weight | 241 gm | 239 gm |
| market maturity: shape according to variety type | straightneck | straightneck |
| market maturity: apex | rounded | rounded |
| market maturity: base | rounded | taper pointed |
| market maturity: ribs | inconspicuous | prominent |
| market maturity: rib furrow depth | shallow | shallow |
| market maturity: rib furrow width | wide | narrow |
| market maturity: fruit surface | smooth | smooth |
| market maturity: warts | none | none |
| market maturity: blossom scar button | slightly extended | raised acorn |
| young fruit: ratio length/maximum diameter (zucchini type varieties) | large (Carlotta) | large |
| young fruit: general shape (zucchini and rounded zucchini type varieties) | cylindrical (Ambassador, Ibis) | cylindrical |
| young fruit: main color of skin (excluding color of ribs or grooves) | green (Elite, Opal, Romano) | green |
| young fruit: intensity of green color of skin (excluding color of ribs or grooves; only varieties with green color of skin) | dark (Arlesa, Sandra, Zefira) | medium |
| general shape | cylindrical | cylindrical |
| length (zucchini type varieties) | long (Carlotta) | very long |
| maximum diameter (zucchini type varieties) | medium (Opal) | medium |
| ratio length/maximum diameter (zucchini type varieties) | large (Carlotta) | large |
| blossom end (zucchini and neck type varieties) | rounded | pointed |
| grooves | absent | absent |
| ribs | present | present |
| protrusion of ribs | very weak (Leda, Tivoli) | strong |
| main color of skin (excluding color of dots, patches, stripes and bands) | green (Ambassador, Baby Bear) | green |
| intensity of green color of skin (only varieties with green color of skin) | dark (Cora) | medium |
| color of ribs compared to main color of skin | same (Grey Zucchini) | darker |
| dots | present (Gold Rush, Table Queen) | present |
| size of main dots | very small (Badger Cross) | small |
| secondary green color between ribs (excluding dots) | absent (Grey Zucchini, Small Sugar) | absent |
| warts on skin | absent | absent |
| size of flower scar | medium (Spidi) | small |
| length of peduncle | medium (Cinderella) | short |
| color of peduncle | green (Ambassador) | green |
| intensity of green color of peduncle | medium (Sunburst) | medium |
| mottling of peduncle | present (Elite) | absent |
| ripe fruit: secondary color of skin (excluding color of mottles, patches, stripes and bands) | cream (Bianchini, Opal) | yellow |
| ripe fruit: intensity of main color of skin (only yellow and orange) | medium | medium |
| ripe fruit: secondary color of skin | green | orange |
| ripe fruit: green hue (only white and cream) | present (Amalthee) | |

TABLE 2-continued

Physiological and Morphological Characteristics of Line ZGN-EH10010

| CHARACTERISTIC | ZGN-EH10010 | Comparison Variety PAYROLL |
|---|---|---|
| ripe fruit: prominence of green hue | medium (Corona) | |
| ripe fruit: color of flesh | yellow (Sunburst, Vegetable Spaghetti) | cream |
| ripe fruit: lignified rind | present (Elite, Little Gem, Scallopini, Yellow Summer Crookneck) | present |
| ripe fruit: structure of flesh | fibrous (Vegetable Spaghetti) | fibrous |
| 10. Rind | | |
| average thickness at medial | 1.6 mm | 1.9 mm |
| toughness | hard | hard |
| overall color pattern | regular | regular |
| main or ground color | green | bronze |
| main or ground color (RHS Color Chart) | N189A | 139A |
| color of blotches | orange | |
| color of blotches (RHS Color Chart) | 20A | |
| 11. Flesh | | |
| average blossom end thickness | 43.3 mm | 22 mm |
| average medial thickness | 42.9 mm | 59 mm |
| average stem end thickness | 42.3 mm | 27.4 mm |
| texture (fine, granular, lumpy or stringy) | fine | fine |
| texture (soft, firm or brittle) | soft | soft |
| texture (dry, moist or juicy) | dry | moist |
| flavor | insipid | slightly sweet |
| quality | good | good |
| color | creamy white | creamy white |
| color (RHS Color Chart) | 150D | 151B |
| 12. Seed Cavity | | |
| average length | 32.2 cm | 28.85 cm |
| average width | 4.4 cm | 5 cm |
| location | conforms to fruit shape | conforms to fruit shape |
| placental tissue | abundant | abundant |
| center core | inconspicuous | inconspicuous |
| 13. Fruit Stalks | | |
| average length | 2.4 cm | 2.75 cm |
| average diameter | 1.6 cm | 2.05 cm |
| cross-section shape | irregular | irregular |
| twisting | twisted | twisted |
| tapering | tapered | tapered |
| straightness | slightly curved | curved |
| texture | spongy | soft |
| furrows | shallow | deep |
| surface | smooth | rough |
| attachment end | slightly expanded | slightly expanded |
| detaches | easily | easily |
| color | dark green | medium green |
| color (RHS Color Chart) | 139A | 137B |
| 14. Seeds | | |
| average length | 14.7 mm | 14.4 mm |
| average width | 8.6 mm | 8.5 mm |
| average thickness | 3.2 mm | 2.75 mm |
| face surface | smooth | smooth |
| color | cream | white |
| color (RHS Color Chart) | 158D | 155A |
| luster | glossy | dull |
| margin | curved | curved |
| margin edge | rounded | rounded |
| separation from pulp | easy | easy |
| average grams per 100 seeds | 10.8 gm | 13.75 gm |
| average number of seeds per fruit | 56 | 187 |
| seed coat | normal | normal |
| size | medium (Diamant) | small |
| shape | broad elliptical (Baby Boo) | elliptic |
| hull | present (Baby Bear, Elite) | present |

TABLE 2-continued

Physiological and Morphological Characteristics of Line ZGN-EH10010

| CHARACTERISTIC | ZGN-EH10010 | Comparison Variety PAYROLL |
|---|---|---|
| appearance of hull | fully developed (Elite) | fully developed |
| color of hull | cream (De Nice à Fruit Rond) | cream |
| fruit type: | zucchini | |
| fruit: patches, stripes or bands in ripe stage (if zucchini type) | present (Elite, Greyzini) | |

*These are typical values. Values may vary due to environment. Other values that are substantially equivalent are also within the scope of the invention.

TABLE 3

Physiological and Morphological Characteristics of Line LEB-EH-08-001

| | Characteristic | LEB-EH-08-001 | Comparison Variety Anita |
|---|---|---|---|
| 1. | Species | *Pepo* | *Pepo* |
| 2. | Kind/Use | squash | squash |
| 3. | Type | summer (vegetable marrow) | summer |
| 4. | Cotyledon | | |
| | length | 45.65 mm | 51.9 mm |
| | width | 29.21 mm | 30.5 mm |
| | apex | tapered | rounded |
| | veining | plainly visible | plainly visible |
| | color | medium green | light green |
| | color (RHS Color Chart) | 137A | 137B |
| | Seedling | | |
| | shape of cotyledons | elliptic (Cora, Tivoli) | elliptic |
| | intensity of green color of cotyledons | medium (Cora) | light |
| | cross section of cotyledons | concave | straight |
| 5. | Mature Plant | | |
| | growth habit | semi-bush | bush |
| | plant type | glabrous | prickly |
| 6. | Main Stem | | |
| | cross-section shape | round | round |
| | average diameter at mid-point of 1st internode | 27.96 mm | 29.2 mm |
| | average length | 37.53 cm | 31.6 cm |
| | average number of internodes | 19.5 | 23.5 |
| | Stem | | |
| | color | partly green and partly yellow (Autumn Gold) | partly green and partly yellow |
| | intensity of green color | dark (Greyzini) | medium |
| | mottling | absent (Cinderella) | present |
| | tendrils | well developed (Baby Bear, Greyzini) | absent to rudimentary |
| | Plant | | |
| | growth habit | bush (Greyzini) | bush |
| | branching | absent (Goldi) | absent |
| | bush varieties only: attitude of petiole (excluding lower external leaves) | semi-erect (Arlesa) | semi-erect |
| 7. | Leaves | | |
| | blade shape | reniform | reniform |
| | blade form | deep lobed | deep lobed |
| | margin | dentate | denticulate |
| | margin edges | frilled | frilled |
| | average width | 40.5 cm | 36.8 cm |
| | average length | 36.75 cm | 29 cm |
| | leaf surface | blistered | blistered |
| | dorsal surface pubescence | bristled | soft hairy |
| | vental surface pubescence | bristled | soft hairy |
| | color | medium green | dark green |
| | color (RHS Color Chart) | 139A | 139A |
| | leaf blotching | blotched with gray | blotched with gray |
| | leaf blade: size | medium (Ambassador) | large |

TABLE 3-continued

Physiological and Morphological Characteristics of Line LEB-EH-08-001

| | Characteristic | LEB-EH-08-001 | Comparison Variety Anita |
|---|---|---|---|
| | leaf blade: incisions | medium (Jackpot) | medium |
| | leaf blade: intensity of green color of upper surface | medium (Cora) | dark |
| | leaf blade: silvery patches | present (Civac) | present |
| | leaf blade: relative area covered by silvery patches | very small (Albo) | medium |
| | average petiole length | 42.41 cm | 33.05 cm |
| | petiole length | long (Autumn Gold, Baikal) | medium |
| | petiole: number of prickles | medium (Spidy) | medium |
| 8. | Flower | | |
| | pistillate flower: diameter | 12.61 cm | 13.7 cm |
| | pistillate flower: ovary | drum-like | drum-like |
| | pistillate flower: average pedicel length | 2.02 cm | 2 cm |
| | pistillate flower: margin shape | curved | curved |
| | pistillate flower: margin edges | frilled | plain |
| | pistillate flower: average sepal width | 1.38 mm | 1.5 mm |
| | pistillate flower: average sepal length | 4.55 mm | 6.5 mm |
| | pistillate flower: color | orange | deep yellow |
| | pistillate flower: color (RHS Color Chart) | 23A | 17A |
| | staminate flower: average sepal length | 15.03 mm | 16.3 mm |
| | staminate flower: average sepal width | 2.43 mm | 2.5 mm |
| | staminate flower: average pedicel length | 149 mm | 147 mm |
| | staminate flower: color | orange | deep yellow |
| | female flower: ring at inner side of corolla | present (Aurore) | present |
| | female flower: color of ring at inner side of corolla | green (Aurore, Early White Bush Scallop, President) | green |
| | female flower: intensity of green color of ring at inner side of corolla (varieties with green ring at inner side of corolla) | medium (Samba, Senator) | medium |
| | male flower: ring at inner side of corolla | present (Goldi) | present |
| | male flower: color of ring at inner side of corolla | green (Austral, Belor, Goldi) | green |
| | male flower: intensity of green color of ring at inner side of corolla (varieties with green ring at inner side of corolla) | medium (Verdi) | medium |
| | staminate flower: color | 25A | 21A |
| 9. | Fruit | | |
| | market maturity: average length | 14.35 cm | 12.4 cm |
| | market maturity: average width - stem end | 4.72 cm | 3.8 cm |
| | market maturity: average width - blossom end | 5.12 cm | 4.6 cm |
| | market maturity: average weight | 296.5 gm | 208.4 gm |
| | market maturity: shape according to variety type | straightneck | straightneck |
| | market maturity: apex | rounded | taper pointed |
| | market maturity: base | flattened | flattened |
| | market maturity: ribs | inconspicuous | inconspicuous |
| | market maturity: rib furrow depth | shallow | shallow |
| | market maturity: rib furrow width | wide | narrow |
| | market maturity: fruit surface | smooth | smooth |
| | market maturity: warts | none | none |
| | market maturity: blossom scar button | raised acorn | raised acorn |

TABLE 3-continued

Physiological and Morphological Characteristics of Line LEB-EH-08-001

| Characteristic | LEB-EH-08-001 | Comparison Variety Anita |
|---|---|---|
| young fruit: ratio length/maximum diameter (zucchini type varieties) | medium (Cora) | small |
| young fruit: general shape (zucchini and rounded zucchini type varieties) | tapered elliptical (Top Kapi) | pear shaped |
| young fruit: main color of skin (excluding color of ribs or grooves) | green (Elite, Opal, Romano) | partly white and partly green |
| young fruit: intensity of green color of skin (excluding color of ribs or grooves; only varieties with green color of skin) | light (Arlika) | light |
| general shape | club shaped | pear shaped |
| length (zucchini type varieties) | short (Jedida) | short |
| maximum diameter (zucchini type varieties) | medium (Opal) | large |
| ratio length/maximum diameter (zucchini type varieties) | medium (Cora) | medium |
| blossom end (zucchini and neck type varieties) | rounded | rounded |
| grooves | absent | absent |
| ribs | present | present |
| protrusion of ribs | weak (Ambassador) | weak |
| main color of skin (excluding color of dots, patches, stripes and bands) | green (Ambassador, Baby Bear) | green |
| intensity of green color of skin (excluding color of dots, patches, stripes and bands; varieties with green color or skin) | light | very light |
| color of ribs compared to main color of skin (excluding color of dots, patches, stripes and bands) | same (Grey Zucchini) | same |
| dots | present (Gold Rush, Table Queen) | present |
| size of main dots | small (Ambassador) | large |
| secondary green color between ribs (excluding dots) | absent (Grey Zucchini, Small Sugar) | |
| warts on skin | absent | absent |
| size of flower scar | small (Goldi) | medium |
| length of peduncle | medium (Cinderella) | long |
| color of peduncle | green (Ambassador) | green |
| intensity of green color of peduncle | medium (Sunburst) | medium |
| mottling of peduncle | absent (Sunburst) | present |
| ripe fruit: main color of skin (excluding color of mottles, patches, stripes and bands) | yellow (Gold Rush) | yellow |
| ripe fruit: intensity of main color of skin (only yellow and orange) | medium | dark |
| ripe fruit: color of flesh | cream (Elite) | yellow |
| ripe fruit: lignified rind | present (Elite, Little Gem, Scallopini, Yellow Summer Crookneck) | present |
| ripe fruit: structure of flesh | fibrous (Vegetable Spaghetti) | fibrous |
| 10. Rind | | |
| average thickness at medial | 3.15 mm | 3.1 mm |
| toughness | hard | hard |
| overall color pattern | regular | irregular |
| main or ground color | yellow | creamy-yellow |
| main or ground color (RHS Color Chart) | 12B | 20C |
| 11. Flesh | | |
| average blossom end thickness | 11.21 mm | 14.4 mm |
| average medial thickness | 73.43 mm | 78.9 mm |

TABLE 3-continued

Physiological and Morphological Characteristics of Line LEB-EH-08-001

| Characteristic | LEB-EH-08-001 | Comparison Variety Anita |
|---|---|---|
| average stem end thickness | 17.3 mm | 17.6 mm |
| texture (fine, granular, lumpy or stringy) | fine | stringy |
| texture (soft, firm or brittle) | firm | firm |
| texture (dry, moist or juicy) | dry | moist |
| flavor | slightly sweet | insipid |
| quality | good | good |
| color | yellowish-green | cream |
| color (RHS Color Chart) | 154A | 155C |
| 12. Seed Cavity | | |
| average length | 22.9 cm | 28.1 cm |
| average width | 8.05 cm | 10.1 cm |
| location | conforms to fruit shape | conforms to fruit shape |
| placental tissues | abundant | abundant |
| center core | inconspicuous | prominent |
| 13. Fruit Stalks | | |
| average length | 3.54 cm | 3.3 cm |
| average diameter | 2.09 cm | 2.5 cm |
| cross-section shape | irregular | irregular |
| twisting | not twisted | not twisted |
| tapering | not tapered | not tapered |
| straightness | slightly curved | straight |
| texture | hard | spongy |
| furrows | deep | deep |
| surface | rough | spiny |
| attachment end | expanded | not expanded |
| detaches | easily | easily |
| color | medium green | medium green |
| color (RHS Color Chart) | 138A | 144B |
| 14. Seeds | | |
| average length | 13.95 mm | 16.3 mm |
| average width | 8.3 mm | 9.15 mm |
| average thickness | 3.55 mm | 2.5 mm |
| face surface | smooth | smooth |
| color | white | cream |
| color (RHS Color Chart) | 155A | 162C |
| luster | dull | dull |
| margin | curved | straight |
| margin edge | rounded | rounded |
| separation from pulp | easy | easy |
| average grams per 100 seeds | 13.35 gm | 16.5 gm |
| average number of seeds per fruit | 300.5 | 346.5 |
| seed coat | normal | normal |
| size | small (Delicata) | large |
| shape | elliptic (Elite) | broad elliptic |
| hull | present (Baby Bear, Elite) | present |
| appearance of hull | fully developed (Elite) | rudimentary |
| color of hull | cream (De Nice à Fruit Rond) | cream |
| 15 Special Conditions for the Examination of the Variety | | |
| fruit: type | rounded zucchini | |
| if zucchini type: patches, stripes or bands in ripe stage | absent (Ambassador, Black Jack) | |

*These are typical values. Values may vary due to environment. Other values that are substantially equivalent are also within the scope of the invention.

C. BREEDING SQUASH PLANTS

One aspect of the current invention concerns methods for producing seed of squash hybrid SV0104YL involving crossing squash lines ZGN-EH10010 and LEB-EH-08-001. Alternatively, in other embodiments of the invention, hybrid SV0104YL, line ZGN-EH10010, or line LEB-EH-08-001 may be crossed with itself or with any second plant. Such methods can be used for propagation of hybrid SV0104YL and/or the squash lines ZGN-EH10010 and LEB-EH-08-001, or can be used to produce plants that are derived from hybrid SV0104YL and/or the squash lines ZGN-EH10010 and LEB-EH-08-001. Plants derived from hybrid SV0104YL and/or the squash lines ZGN-EH10010 and LEB-EH-08-001 may be used, in certain embodiments, for the development of new squash varieties.

The development of new varieties using one or more starting varieties is well known in the art. In accordance with the invention, novel varieties may be created by crossing hybrid SV0104YL followed by multiple generations of breeding according to such well known methods. New varieties may be created by crossing with any second plant. In selecting such a second plant to cross for the purpose of developing novel lines, it may be desired to choose those plants which either themselves exhibit one or more selected desirable characteristics or which exhibit the desired characteristic(s) when in hybrid combination. Once initial crosses have been made, inbreeding and selection take place to produce new varieties. For development of a uniform line, often five or more generations of selfing and selection are involved.

Uniform lines of new varieties may also be developed by way of double-haploids. This technique allows the creation of true breeding lines without the need for multiple generations of selfing and selection. In this manner true breeding lines can be produced in as little as one generation. Haploid embryos may be produced from microspores, pollen, anther cultures, or ovary cultures. The haploid embryos may then be doubled autonomously, or by chemical treatments (e.g. colchicine treatment). Alternatively, haploid embryos may be grown into haploid plants and treated to induce chromosome doubling. In either case, fertile homozygous plants are obtained. In accordance with the invention, any of such techniques may be used in connection with a plant of the invention and progeny thereof to achieve a homozygous line.

Backcrossing can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny have the characteristic being transferred, but are like the superior parent for most or almost all other loci. The last backcross generation would be selfed to give pure breeding progeny for the trait being transferred.

The plants of the present invention are particularly well suited for the development of new lines based on the elite nature of the genetic background of the plants. In selecting a second plant to cross with SV0104YL and/or squash lines ZGN-EH10010 and LEB-EH-08-001 for the purpose of developing novel squash lines, it will typically be preferred to choose those plants which either themselves exhibit one or more selected desirable characteristics or which exhibit the desired characteristic(s) when in hybrid combination. Examples of desirable traits may include, in specific embodiments, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of squash plants developed by this invention.

D. PERFORMANCE CHARACTERISTICS

As described above, hybrid SV0104YL exhibits desirable traits, as conferred by squash lines ZGN-EH10010 and LEB-EH-08-001. The performance characteristics of hybrid SV0104YL and squash lines ZGN-EH10010 and LEB-EH-08-001 were the subject of an objective analysis of the performance traits relative to other varieties. The results of the analysis are presented below.

TABLE 4

Performance Data of Hybrid SV0104YL.

| ASRT3 | fruit shape | fruit color | fruit uniformity | blossom scar size | ease of harvest | viral severity | vigor | growth habit | spines | marketable fruit/plant |
|---|---|---|---|---|---|---|---|---|---|---|
| ESKENDERANY | 8 | 8 | 8 | 3 | 2 | 9 | 5 | 5 | 6 | 1.6 |
| ESKENDERANY | 8 | 8 | 9 | 4 | 1 | 9 | 5 | 3 | 8 | 2.9 |
| ESKENDERANY | 7 | 6 | 8 | 5 | 1 | 9 | 6 | 3 | 8 | 3.4 |
| ESKENDERANY | 5 | 5 | 6 | 4 | 1 | 8 | 6 | 3 | 8 | 6.6 |
| LEBEHH0104 | 4 | 4 | 3 | 5 | 1 | 2 | 5 | 5 | 7 | 4.8 |
| LEBEHH0104 | 3 | 4 | 3 | 4 | 1 | 2 | 4 | 4 | 5 | 5.8 |
| LEBEHH0104 | 4 | 5 | 4 | 5 | 2 | 1 | 4 | 7 | 7 | 6.3 |
| LEBEHH0104 | 4 | 5 | 6 | 5 | 1 | 2 | 4 | 5 | 6 | 6.4 |

Qualitative and quantitative (yield) observations from a randomized, repicated trial in Jordan from July, 2012.
Qualitative traits are on a 1-9 scale where 1 is ideal, 5 is acceptable, and 9 is totally unacceptable.
Marketable fruits/plant is based on 11 harvest dates over 26 days, in an openfield environment with moderate pressure of potyvirus and geminivirus diseases.
Eskenderany is the most similar commercial hybrid included in the trial set.

E. FURTHER EMBODIMENTS OF THE INVENTION

In certain aspects of the invention, plants described herein are provided modified to include at least a first desired heritable trait. Such plants may, in one embodiment, be developed by a plant breeding technique called backcrossing, wherein essentially all of the morphological and physiological characteristics of a variety are recovered in addition to a genetic locus transferred into the plant via the backcrossing technique. The term single locus converted plant as used herein refers to those squash plants which are developed by a plant breeding technique called backcrossing, wherein essentially all of the morphological and physiological characteristics of a variety are recovered in addition to the single locus transferred into the variety via the backcrossing technique. By essentially all of the morphological and physiological characteristics, it is meant that the characteristics of a plant are recovered that are otherwise present when compared in the same environment, other than an occasional variant trait that might arise during backcrossing or direct introduction of a transgene.

Backcrossing methods can be used with the present invention to improve or introduce a characteristic into the present variety. The parental squash plant which contributes the locus for the desired characteristic is termed the nonrecurrent or donor parent. This terminology refers to the fact that the nonrecurrent parent is used one time in the backcross protocol and therefore does not recur. The parental squash plant to which the locus or loci from the nonrecurrent parent are transferred is known as the recurrent parent as it is used for several rounds in the backcrossing protocol.

In a typical backcross protocol, the original variety of interest (recurrent parent) is crossed to a second variety (non-recurrent parent) that carries the single locus of interest to be transferred. The resulting progeny from this cross are then crossed again to the recurrent parent and the process is repeated until a squash plant is obtained wherein essentially all of the morphological and physiological characteristics of the recurrent parent are recovered in the converted plant, in addition to the single transferred locus from the nonrecurrent parent.

The selection of a suitable recurrent parent is an important step for a successful backcrossing procedure. The goal of a backcross protocol is to alter or substitute a single trait or characteristic in the original variety. To accomplish this, a single locus of the recurrent variety is modified or substituted with the desired locus from the nonrecurrent parent, while retaining essentially all of the rest of the desired genetic, and therefore the desired physiological and morphological constitution of the original variety. The choice of the particular nonrecurrent parent will depend on the purpose of the backcross; one of the major purposes is to add some commercially desirable trait to the plant. The exact backcrossing protocol will depend on the characteristic or trait being altered and the genetic distance between the recurrent and nonrecurrent parents. Although backcrossing methods are simplified when the characteristic being transferred is a dominant allele, a recessive allele, or an additive allele (between recessive and dominant), may also be transferred. In this instance it may be necessary to introduce a test of the progeny to determine if the desired characteristic has been successfully transferred.

In one embodiment, progeny squash plants of a backcross in which a plant described herein is the recurrent parent comprise (i) the desired trait from the non-recurrent parent and (ii) all of the physiological and morphological characteristics of squash the recurrent parent as determined at the 5% significance level when grown in the same environmental conditions.

New varieties can also be developed from more than two parents. The technique, known as modified backcrossing, uses different recurrent parents during the backcrossing. Modified backcrossing may be used to replace the original recurrent parent with a variety having certain more desirable characteristics or multiple parents may be used to obtain different desirable characteristics from each.

With the development of molecular markers associated with particular traits, it is possible to add additional traits into an established germ line, such as represented here, with the end result being substantially the same base germplasm with the addition of a new trait or traits. Molecular breeding, as described in Moose and Mumm, 2008 (Plant Physiology, 147: 969-977), for example, and elsewhere, provides a mechanism for integrating single or multiple traits or QTL into an elite line. This molecular breeding-facilitated movement of a trait or traits into an elite line may encompass incorporation of a particular genomic fragment associated with a particular trait of interest into the elite line by the mechanism of identification of the integrated genomic fragment with the use of flanking or associated marker assays. In the embodiment represented here, one, two, three or four genomic loci, for example, may be integrated into an elite line via this methodology. When this elite line containing the additional loci is further crossed with another parental elite line to produce hybrid offspring, it is possible to then incorporate at least eight separate additional loci into the hybrid. These additional loci may confer, for example, such traits as a disease resistance or a fruit quality trait. In one embodiment, each locus may confer a separate trait. In another embodiment, loci may need to be homozygous and exist in each parent line to confer a trait in the hybrid. In yet another embodiment, multiple loci may be combined to confer a single robust phenotype of a desired trait.

Many single locus traits have been identified that are not regularly selected for in the development of a new inbred but that can be improved by backcrossing techniques. Single locus traits may or may not be transgenic; examples of these traits include, but are not limited to, herbicide resistance, resistance to bacterial, fungal, or viral disease, insect resistance, modified fatty acid or carbohydrate metabolism, and altered nutritional quality. These comprise genes generally inherited through the nucleus.

Direct selection may be applied where the single locus acts as a dominant trait. For this selection process, the progeny of the initial cross are assayed for viral resistance and/or the presence of the corresponding gene prior to the backcrossing. Selection eliminates any plants that do not have the desired gene and resistance trait, and only those plants that have the trait are used in the subsequent backcross. This process is then repeated for all additional backcross generations.

Selection of squash plants for breeding is not necessarily dependent on the phenotype of a plant and instead can be based on genetic investigations. For example, one can utilize a suitable genetic marker which is closely genetically linked to a trait of interest. One of these markers can be used to identify the presence or absence of a trait in the offspring of a particular cross, and can be used in selection of progeny for continued breeding. This technique is commonly referred to as marker assisted selection. Any other type of genetic marker or other assay which is able to identify the relative presence or absence of a trait of interest in a plant can also be useful for breeding purposes. Procedures for marker assisted selection are well known in the art. Such methods will be of particular utility in the case of recessive traits and variable phenotypes, or where conventional assays may be more expensive, time consuming or otherwise disadvantageous. Types of genetic markers which could be used in accordance with the invention include, but are not necessarily limited to, Simple Sequence Length Polymorphisms (SSLPs) (Williams et al., *Nucleic Acids Res.*, 1 8:6531-6535, 1990), Randomly Amplified Polymorphic DNAs (RAPDs), DNA Amplification Fingerprinting (DAF), Sequence Characterized Amplified Regions (SCARs), Arbitrary Primed Polymerase Chain Reaction (AP-PCR), Amplified Fragment Length Polymorphisms (AFLPs) (EP 534 858, specifically incorporated herein by reference in its entirety), and Single Nucleotide Polymorphisms (SNPs) (Wang et al., *Science*, 280:1077-1082, 1998).

F. PLANTS DERIVED BY GENETIC ENGINEERING

Many useful traits that can be introduced by backcrossing, as well as directly into a plant, are those which are introduced by genetic transformation techniques. Genetic transformation may therefore be used to insert a selected transgene into a plant of the invention or may, alternatively, be used for the preparation of transgenes which can be introduced by backcrossing. Methods for the transformation of plants that are well known to those of skill in the art and applicable to many crop species include, but are not limited to, electroporation, microprojectile bombardment, *Agrobacterium*-mediated transformation and direct DNA uptake by protoplasts.

To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

An efficient method for delivering transforming DNA segments to plant cells is microprojectile bombardment. In this method, particles are coated with nucleic acids and delivered into cells by a propelling force. Exemplary particles include those comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target cells. The screen disperses the particles so that they are not delivered to the recipient cells in large aggregates. Microprojectile bombardment techniques are widely applicable, and may be used to transform virtually any plant species.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. Modern *Agrobacterium* transformation vectors are capable of replication in *E. coli* as well as *Agrobacterium*, allowing for convenient manipulations (Klee et al., *Bio-Technology*, 3(7):637-642, 1985). Moreover, recent technological advances in vectors for *Agrobacterium*-mediated gene transfer have improved the arrangement of genes and restriction sites in the vectors to facilitate the construction of vectors capable of expressing various polypeptide coding genes. The vectors described have convenient multi-linker regions flanked by a promoter and a polyadenylation site for direct expression of inserted polypeptide coding genes. Additionally, *Agrobacterium* containing both armed and disarmed Ti genes can be used for transformation.

In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells is well known in the art (Fraley et al., *Bio/Technology*, 3:629-635, 1985; U.S. Pat. No. 5,563,055).

Transformation of plant protoplasts also can be achieved using methods based on calcium phosphate precipitation, polyethylene glycol treatment, electroporation, and combinations of these treatments (see, e.g., Potrykus et al., *Mol. Gen. Genet.*, 199:183-188, 1985; Omirulleh et al., *Plant Mol. Biol.*, 21(3):415-428, 1993; Fromm et al., *Nature*, 312:791-793, 1986; Uchimiya et al., *Mol. Gen. Genet.*, 204:204, 1986; Marcotte et al., *Nature*, 335:454, 1988). Transformation of plants and expression of foreign genetic elements is exemplified in Choi et al. (*Plant Cell Rep.*, 13: 344-348, 1994), and Ellul et al. (*Theor. Appl. Genet.*, 107:462-469, 2003).

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for plant gene expression include, but are not limited to, the cauliflower mosaic virus (CaMV) P-35S promoter, which confers constitutive, high-level expression in most plant tissues (see, e.g., Odel et al., *Nature*, 313:810, 1985), including in monocots (see, e.g., Dekeyser et al., *Plant Cell*, 2:591, 1990; Terada and Shimamoto, *Mol. Gen. Genet.*, 220:389, 1990); a tandemly duplicated version of the CaMV 35S promoter, the enhanced 35S promoter (P-e35S); 1 the nopaline synthase promoter (An et al., *Plant Physiol.*, 88:547, 1988); the octopine synthase promoter (Fromm et al., *Plant Cell*, 1:977, 1989); and the figwort mosaic virus (P-FMV) promoter as described in U.S. Pat. No. 5,378,619 and an enhanced version of the FMV promoter (P-eFMV) where the promoter sequence of P-FMV is duplicated in tandem; the cauliflower mosaic virus 19S promoter; a sugarcane bacilliform virus promoter; a commelina yellow mottle virus promoter; and other plant DNA virus promoters known to express in plant cells.

A variety of plant gene promoters that are regulated in response to environmental, hormonal, chemical, and/or developmental signals can also be used for expression of an operably linked gene in plant cells, including promoters regulated by (1) heat (Callis et al., *Plant Physiol.*, 88:965, 1988), (2) light (e.g., pea rbcS-3A promoter, Kuhlemeier et al., *Plant Cell*, 1:471, 1989; maize rbcS promoter, Schaffner and Sheen, *Plant Cell*, 3:997, 1991; or chlorophyll a/b-binding protein promoter, Simpson et al., *EMBO* 1, 4:2723, 1985), (3) hormones, such as abscisic acid (Marcotte et al., *Plant Cell*, 1:969, 1989), (4) wounding (e.g., wun1, Siebertz et al., *Plant Cell*, 1:961, 1989); or (5) chemicals such as methyl jasmonate, salicylic acid, or Safener. It may also be advantageous to employ organ-specific promoters (e.g., Roshal et al., *EMBO J*, 6:1155, 1987; Schernthaner et al., *EMBO* 1, 7:1249, 1988; Bustos et al., *Plant Cell*, 1:839, 1989).

Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a squash plant according to the invention. Non-limiting examples of particular genes and corresponding phenotypes one may choose to introduce into a squash plant include one or more genes for insect tolerance, such as a *Bacillus thuringiensis* (B.t.) gene, pest tolerance such as genes for fungal disease control, herbicide tolerance such as genes conferring glyphosate tolerance, and genes for quality improvements such as yield, nutritional enhancements, environmental or stress tolerances, or any desirable changes in plant physiology, growth, development, morphology or plant product(s). For example, structural genes would include any gene that confers insect tolerance including but not limited to a *Bacillus* insect control protein gene as described in WO 99/31248, herein incorporated by reference in its entirety, U.S. Pat. No. 5,689,052, herein incorporated by reference in its entirety, U.S. Pat. Nos.

5,500,365 and 5,880,275, herein incorporated by reference in their entirety. In another embodiment, the structural gene can confer tolerance to the herbicide glyphosate as conferred by genes including, but not limited to *Agrobacterium* strain CP4 glyphosate resistant EPSPS gene (aroA:CP4) as described in U.S. Pat. No. 5,633,435, herein incorporated by reference in its entirety, or glyphosate oxidoreductase gene (GOX) as described in U.S. Pat. No. 5,463,175, herein incorporated by reference in its entirety.

Alternatively, the DNA coding sequences can affect these phenotypes by encoding a non-translatable RNA molecule that causes the targeted inhibition of expression of an endogenous gene, for example via antisense- or cosuppression-mediated mechanisms (see, for example, Bird et al., *Biotech. Gen. Engin. Rev.*, 9:207, 1991). The RNA could also be a catalytic RNA molecule (i.e., a ribozyme) engineered to cleave a desired endogenous mRNA product (see for example, Gibson and Shillito, *Mol. Biotech.*, 7:125, 1997). Thus, any gene which produces a protein or mRNA which expresses a phenotype or morphology change of interest is useful for the practice of the present invention.

G. DEFINITIONS

In the description and tables herein, a number of terms are used. In order to provide a clear and consistent understanding of the specification and claims, the following definitions are provided:

Allele: Any of one or more alternative forms of a gene locus, all of which alleles relate to one trait or characteristic. In a diploid cell or organism, the two alleles of a given gene occupy corresponding loci on a pair of homologous chromosomes.

Backcrossing: A process in which a breeder repeatedly crosses hybrid progeny, for example a first generation hybrid ($F_1$), back to one of the parents of the hybrid progeny. Backcrossing can be used to introduce one or more single locus conversions from one genetic background into another.

Crossing: The mating of two parent plants.

Cross-pollination: Fertilization by the union of two gametes from different plants.

Diploid: A cell or organism having two sets of chromosomes.

Emasculate: The removal of plant male sex organs or the inactivation of the organs with a cytoplasmic or nuclear genetic factor or a chemical agent conferring male sterility.

Enzymes: Molecules which can act as catalysts in biological reactions.

$F_1$ Hybrid: The first generation progeny of the cross of two nonisogenic plants.

Genotype: The genetic constitution of a cell or organism.

Haploid: A cell or organism having one set of the two sets of chromosomes in a diploid.

Linkage: A phenomenon wherein alleles on the same chromosome tend to segregate together more often than expected by chance if their transmission was independent.

Marker: A readily detectable phenotype, preferably inherited in codominant fashion (both alleles at a locus in a diploid heterozygote are readily detectable), with no environmental variance component, i.e., heritability of 1.

Phenotype: The detectable characteristics of a cell or organism, which characteristics are the manifestation of gene expression.

Quantitative Trait Loci (QTL): Quantitative trait loci (QTL) refer to genetic loci that control to some degree numerically representable traits that are usually continuously distributed.

Resistance: As used herein, the terms "resistance" and "tolerance" are used interchangeably to describe plants that show no symptoms to a specified biotic pest, pathogen, abiotic influence or environmental condition. These terms are also used to describe plants showing some symptoms but that are still able to produce marketable product with an acceptable yield. Some plants that are referred to as resistant or tolerant are only so in the sense that they may still produce a crop, even though the plants are stunted and the yield is reduced.

Regeneration: The development of a plant from tissue culture.

Royal Horticultural Society (RHS) color chart value: The RHS color chart is a standardized reference which allows accurate identification of any color. A color's designation on the chart describes its hue, brightness and saturation. A color is precisely named by the RHS color chart by identifying the group name, sheet number and letter, e.g., Yellow-Orange Group 19A or Red Group 41B.

Self-pollination: The transfer of pollen from the anther to the stigma of the same plant.

Single Locus Converted (Conversion) Plant: Plants which are developed by a plant breeding technique called backcrossing, wherein essentially all of the morphological and physiological characteristics of a squash variety are recovered in addition to the characteristics of the single locus transferred into the variety via the backcrossing technique and/or by genetic transformation.

Substantially Equivalent: A characteristic that, when compared, does not show a statistically significant difference (e.g., p=0.05) from the mean.

Tissue Culture: A composition comprising isolated cells of the same or a different type or a collection of such cells organized into parts of a plant.

Transgene: A genetic locus comprising a sequence which has been introduced into the genome of a squash plant by transformation.

H. DEPOSIT INFORMATION

A deposit of squash hybrid SV0104YL and inbred parent lines ZGN-EH10010 and LEB-EH-08-001, disclosed above and recited in the claims, has been made with the American Type Culture Collection (ATCC), 10801 University Blvd., Manassas, Va. 20110-2209. The date of deposit were Oct. 31, 2012, Sep. 11, 2012, and Dec. 19, 2012, respectively. The accession numbers for those deposited seeds of squash hybrid SV0104YL and inbred parent lines ZGN-EH10010 and LEB-EH-08-001 are ATCC Accession No. PTA-13286, ATCC Accession No. PTA-13185, and ATCC Accession No. PTA-13406, respectively. Upon issuance of a patent, all restrictions upon the deposits will be removed, and the deposits are intended to meet all of the requirements of 37 C.F.R. §1.801-1.809. The deposits will be maintained in the depository for a period of 30 years, or 5 years after the last request, or for the effective life of the patent, whichever is longer, and will be replaced if necessary during that period.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

What is claimed is:

1. A squash plant comprising at least a first set of the chromosomes of squash line ZGN-EH10010 or squash line LEB-EH-08-001, a sample of seed of said lines having been deposited under ATCC Accession Number PTA-13185 and ATCC Accession Number PTA-13406, respectively.

2. A seed comprising at least a first set of the chromosomes of squash line ZGN-EH10010 or squash line LEB-EH-08-001, a sample of seed of said lines having been deposited under ATCC Accession Number PTA-13185 and ATCC Accession Number PTA-13406, respectively.

3. The plant of claim 1, which is inbred.

4. The plant of claim 1, which is hybrid.

5. The seed of claim 2, which is inbred.

6. The seed of claim 2, which is hybrid.

7. The plant of claim 4, wherein the hybrid plant is squash hybrid SV0104YL, a sample of seed of said hybrid SV0104YL having been deposited under ATCC Accession Number PTA-13286.

8. The seed of claim 6, defined as a seed of squash hybrid SV0104YL, a sample of seed of said hybrid SV0104YL having been deposited under ATCC Accession Number PTA-13286.

9. The seed of claim 2, defined as a seed of line ZGN-EH10010 or line LEB-EH-08-001.

10. A plant part of the plant of claim 1, said plant part comprising at least a first set of the chromosomes of squash line ZGN-EH10010 or squash line LEB-EH-08-001, a sample of seed of said lines having been deposited under ATCC Accession Number PTA-13185 and ATCC Accession Number PTA-13406, respectively.

11. The plant part of claim 10, further defined as a leaf, an ovule, pollen, a fruit, or a cell.

12. A squash plant having all the physiological and morphological characteristics of the squash plant of claim 7.

13. A tissue culture of regenerable cells of the plant of claim 1, said cells comprising at least a first set of the chromosomes of squash line ZGN-EH10010 or squash line LEB-EH-08-001, a sample of seed of said lines having been deposited under ATCC Accession Number PTA-13185 and ATCC Accession Number PTA-13406, respectively.

14. The tissue culture according to claim 13, comprising cells or protoplasts from a plant part selected from the group consisting of embryos, meristems, cotyledons, pollen, leaves, anthers, roots, root tips, pistil, flower, seed and stalks.

15. A squash plant regenerated from the tissue culture of claim 13.

16. A method of vegetatively propagating the plant of claim 1, said method comprising the steps of:
(a) collecting tissue capable of being propagated from a plant according to claim 1;
(b) cultivating said tissue to obtain proliferated shoots; and
(c) rooting said proliferated shoots to obtain rooted plantlets.

17. The method of claim 16, further comprising growing at least a first plant from said rooted plantlets.

18. A method of introducing a desired trait into a squash line, said method comprising:
(a) crossing a plant of line ZGN-EH10010 or LEB-EH-08-001 with a second squash plant that comprises a desired trait to produce F1 progeny, a sample of seed of said lines having been deposited under ATCC Accession Number PTA-13185 and ATCC Accession Number PTA-13406, respectively;
(b) selecting an F1 progeny that comprises the desired trait;
(c) backcrossing the selected F1 progeny with a plant of line ZGN-EH10010 or LEB-EH-08-001 to produce backcross progeny;
(d) selecting backcross progeny comprising the desired trait; and
(e) repeating steps (c) and (d) three or more times to produce selected fourth or higher backcross progeny that comprise the desired trait and otherwise comprises all of the morphological and physiological characteristics of squash line ZGN-EH10010 or squash line LEB-EH-08-001.

19. A method of producing a plant comprising an added trait, said method comprising introducing a transgene conferring the trait into a plant of hybrid SV0104YL, line ZGN-EH10010 or line LEB-EH-08-001, a sample of seed of said hybrid and lines having been deposited under ATCC Accession Number PTA-13286, ATCC Accession Number PTA-13185, and ATCC Accession Number PTA-13406, respectively.

20. A plant of squash hybrid SV0104YL, squash line ZGN-EH10010 or squash line LEB-EH-08-001, further comprising a transgene, wherein a sample of seed of said hybrid and lines has been deposited under ATCC Accession Number PTA-13286, ATCC Accession Number PTA-13185, and ATCC Accession Number PTA-13406, respectively, and wherein said plant otherwise comprises all of the morphological and physiological characteristics of squash hybrid SV0104YL, squash line ZGN-EH10010 or squash line LEB-EH-08-001.

21. The plant of claim 20, wherein the transgene confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

22. A plant produced by introducing by backcrossing a single locus conversion into a plant of squash line ZGN-EH10010 or squash line LEB-EH-08-001, wherein said backcrossing is sufficient to produce a plant comprising the single locus conversion and otherwise all of the morphological and physiological characteristics of squash line ZGN-EH10010 or squash line LEB-EH-08-001, and wherein sample of seed of said lines has been deposited under ATCC Accession Number PTA-13185 and ATCC Accession Number PTA-13406, respectively.

23. The plant of claim 22, wherein the single locus conversion confers a trait selected from the group consisting of male sterility, herbicide tolerance, insect resistance, pest resistance, disease resistance, modified fatty acid metabolism, environmental stress tolerance, modified carbohydrate metabolism and modified protein metabolism.

24. A method for producing a seed of a plant derived from at least one of hybrid SV0104YL, line ZGN-EH10010 or line LEB-EH-08-001, said method comprising the steps of:
(a) crossing a squash plant of hybrid SV0104YL, line ZGN-EH10010 or line LEB-EH-08-001 with itself or a second squash plant; a sample of seed of said hybrid and lines having been deposited under ATCC Accession Number PTA-13286, ATCC Accession Number PTA-13185, and ATCC Accession Number PTA-13406, respectively; and
(b) allowing seed of a hybrid SV0104YL, line ZGN-EH10010 or line LEB-EH-08-001-derived squash plant to form.

25. The method of claim 24, further comprising the steps of:
(c) selfing a plant grown from said hybrid SV0104YL, ZGN-EH10010 or LEB-EH-08-001-derived squash seed to yield additional hybrid SV0104YL, line ZGN-EH10010 or line LEB-EH-08-001-derived squash seed;

(d) growing said additional hybrid SV0104YL, line ZGN-EH10010 or line LEB-EH-08-001-derived squash seed of step (c) to yield additional hybrid SV0104YL, line ZGN-EH10010 or line LEB-EH-08-001-derived squash plants; and (e) repeating the crossing and growing steps of (c) and (d) to generate at least a first further hybrid SV0104YL, line ZGN-EH10010 or line LEB-EH-08-001-derived squash plant.

26. The method of claim 24, wherein the second squash plant is of an inbred squash line.

27. The method of claim 24, comprising crossing line ZGN-EH10010 with line LEB-EH-08-001, a sample of seed of said lines having been deposited under ATCC Accession Number PTA-13185, and ATCC Accession Number PTA-13406, respectively.

28. The method of claim 25, further comprising:
(f) crossing the further hybrid SV0104YL, ZGN-EH10010 or LEB-EH-08-001-derived squash plant with a second squash plant to produce seed of a hybrid progeny plant.

29. A plant part of the plant of claim 7, wherein the plant part comprises a cell of zucchini hybrid SV0104YL.

30. The plant part of claim 29, further defined as a leaf, a flower, a fruit, an ovule, pollen, or a cell.

31. A method of producing a squash seed, said method comprising crossing the plant of claim 1 with itself or a second squash plant and allowing seed to form.

32. A method of producing a squash fruit, said method comprising:
(a) obtaining a plant according to claim 1, wherein the plant has been cultivated to maturity; and
(b) collecting a squash from the plant.

* * * * *